United States Patent [19]

Stine et al.

[11] Patent Number: 5,491,277
[45] Date of Patent: Feb. 13, 1996

[54] MIXED-PHASE SOLID BED HYDROCARBON ALKYLATION PROCESS

[75] Inventors: Laurence O. Stine; Harold U. Hammershaimb, both of Western Springs; Joseph A. Kocal, Gurnee, all of Ill.

[73] Assignee: UOP, Des Plaines, Ill.

[21] Appl. No.: 174,494

[22] Filed: Dec. 28, 1993

[51] Int. Cl.$^6$ ........................................ C07C 2/62
[52] U.S. Cl. .......................... 585/719; 585/722; 585/467
[58] Field of Search ...................... 585/719, 722, 585/467

[56] References Cited

U.S. PATENT DOCUMENTS

| | | | |
|---|---|---|---|
| 3,893,942 | 7/1979 | Yang | 252/411 |
| 4,008,291 | 2/1977 | Zabransky et al. | 585/722 |
| 4,139,573 | 2/1979 | Carson | 260/683.49 |
| 4,540,831 | 9/1985 | Briggs | 568/697 |
| 4,849,569 | 7/1989 | Smith, Jr. | 585/446 |
| 4,950,834 | 8/1990 | Arganbright et al. | 585/446 |
| 5,157,196 | 10/1992 | Crossland et al. | 585/720 |
| 5,190,730 | 3/1993 | Smith, Jr. et al. | 422/109 |

*Primary Examiner*—Asok Pal
*Attorney, Agent, or Firm*—Thomas K. McBride; John F. Spears, Jr.

[57] ABSTRACT

Paraffins and other hydrocarbons are alkylated using a solid bed catalyst in a process featuring a reaction zone operated at mixed-phase conditions which allow the heat of reaction to vaporize a portion of the liquid phase feed hydrocarbon passing downward through it thus facilitating recycling of the feed hydrocarbon. The feed hydrocarbon recovered from the reaction zone effluent is recycled as a liquid, preferably admixed with hydrogen, with the feed olefin being preferably introduced near the top of the reactor as a vapor. The catalyst preferably contains a metal hydrogenation function effective to selectively hydrogenate $C_6$-plus olefins produced as by-products.

13 Claims, 1 Drawing Sheet

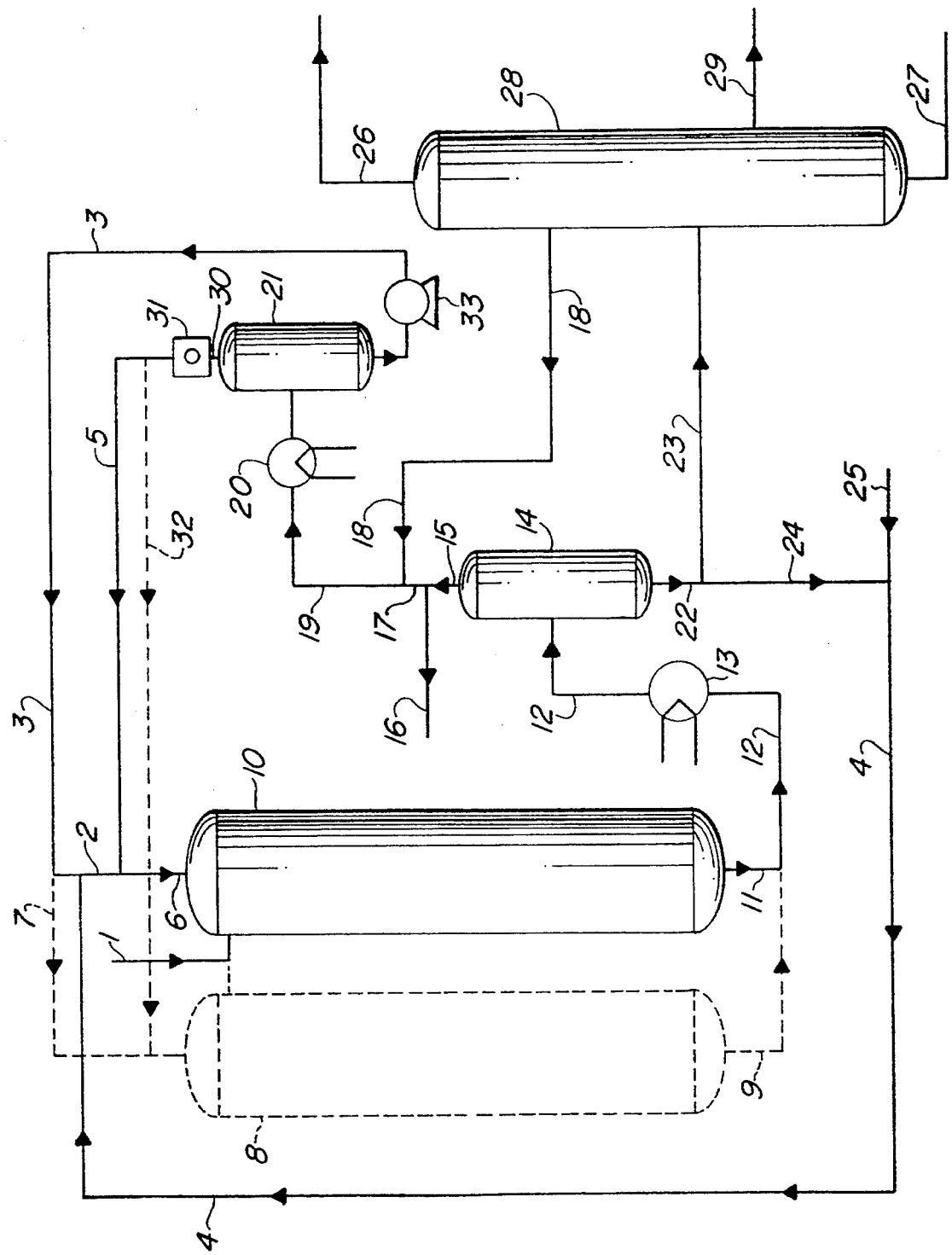

MIXED-PHASE SOLID BED HYDROCARBON ALKYLATION PROCESS

BACKGROUND OF THE INVENTION

1. Field of the Invention

The invention relates to a hydrocarbon conversion process. The invention specifically relates to the alkylation of hydrocarbons such as aromatics or paraffins to produce useful chemicals and motor fuel. The invention is primarily directed to a process for the solid bed alkylation of isobutane to produce $C_8$ isoparaffins useful as motor fuel blending components.

2. Related Art

Large amounts of high octane gasoline are produced by alkylation of isobutane with butenes or propylene. This significantly increases the value of the $C_4$ feed hydrocarbons. Large amounts of valuable aromatic hydrocarbons including cumene, ethylbenzene and $C_{10}$-$C_{15}$ linear alkylaromatics are produced by the alkylation of benzene with olefins of the appropriate carbon number.

The variety of possible feed reactants and the passage of time has led to the development of a number of effective alkylation technologies which are employed in large scale commercial facilities. One of the most widely used processes for the production of motor fuel is HF alkylation as described in U.S. Pat. No. 4,139,573 issued to D. B. Carson. This reference provides an overview of the HF alkylation process and also describes the use of indirect heat exchange to vaporize butanes as a means to remove heat from the reaction zone.

U.S. Pat. No. 3,893,942 issued to C. Yang discloses a method of increasing the stability of zeolitic alkylation catalysts by including a Group VIII metal hydrogenation agent and periodically hydrogenating partially deactivated catalyst by contact with a hydrogen containing gas.

U.S. Pat. No. 4,849,569 issued to L. A. Smith, Jr. describes a solid bed alkylation process employing catalytic distillation to react a $C_2$-$C_{10}$ olefin with an aromatic hydrocarbon. In catalytic distillation the heat of reaction is allowed to vaporize a portion of the liquid phase reactants present in the reaction zone thus removing heat from the reaction zone. This reference describes the use of aluminosilicate molecular sieves as a catalyst. U.S. Pat. No. 4,950,834 issued to R. P. Arganbright et al. describes the production of cumene by the reaction of propylene and benzene using solid catalysts in a catalytic distillation zone. The two catalysts may contain Y zeolite or omega zeolite.

Yet another design for a solid catalyst alkylation process is described in U.S. Pat. No. 5,157,196. This process uses a moving bed of catalyst, with the catalyst being loaded with a paraffin substrate outside of the reactor and then passing through the reactor and into a product recovery zone to produce motor fuel alkylate.

U.S. Pat. No. 5,190,730 issued to L. A. Smith, Jr. et al. provides a process in which the heat released by an exothermic oligomerization or etherification reaction is used to vaporize reactants. The reactants are preheated and passed through a plug flow prereactor at conditions such that any heat released by the reaction will cause vaporization of reactants. That is, this prereactor is maintained at the boiling point of the reaction mixture, which allows the temperature of the reactor to be regulated by adjustments to the reactor pressure.

U.S. Pat. No. 4,540,831 issued to B. A. Briggs presents a similar reaction system in which a bed of catalyst within a reaction vessel is maintained at a pressure which allows heat released by an exothermic reaction to vaporize reactants, with the vapors being condensed by an internal overhead condenser and returned to the catalyst bed for withdrawal from the bottom of the vessel.

BRIEF SUMMARY OF THE INVENTION

The invention is a solid catalyst alkylation process operated at a pressure which allows vaporization of a reactant to control the temperature of the reaction zone. The invention is also characterized by a unique process flow in which the hydrocarbon substrate leaving the reaction zone is recycled to the reactor, preferably in admixture with hydrogen employed to selectively hydrogenate $C_6$-plus olefins formed within the reactor. The olefinic reactant is preferably passed into the reactor as a vapor to reduce the inlet olefin concentration in the liquid on the catalyst. Controlling the vapor-liquid distribution of the olefin in this way can increase the paraffin/olefin ratio at the surface of the catalyst.

One broad embodiment of the invention may be characterized as a process for the alkylation of a feed hydrocarbon which comprises the steps of passing a first feed stream comprising a feed hydrocarbon and a second feed stream comprising an alkylating agent into the upper end of a reaction zone containing a fixed bed of solid alkylation catalyst and operated at alkylation-promoting conditions which include an inlet pressure and temperature which result in mixed-phase conditions in which at least a portion of the alkylating agent and the feed hydrocarbon is present as a vapor and reacting the feed hydrocarbon and the olefinic hydrocarbon to produce a product hydrocarbon in an exothermic reaction which causes the vaporization of liquid phase hydrocarbons present in the reaction zone; passing a mixed-phase effluent stream comprising said feed hydrocarbon and said product hydrocarbon, and which is withdrawn from the reaction zone, into a separation zone in which the effluent stream is separated into a liquid phase process stream, which comprises the product hydrocarbon, and a vapor phase process stream, which comprises hydrogen and is rich in the feed hydrocarbon; passing a first portion of the liquid phase process stream into a product recovery zone, and recovering the product hydrocarbon; recovering hydrogen from the vapor phase process stream, and passing at least a minor portion of the thus recovered hydrogen into the reaction zone; recovering at least a major portion of the feed hydrocarbon from the vapor phase process stream and passing the thus recovered feed hydrocarbon into the reaction zone. Preferably a second reaction zone is undergoing regeneration during this sequence and the regenerent media from the second reaction zone is admixed with the effluent of the on-stream reaction zone.

BRIEF SUMMARY OF THE DRAWING

The drawing is a flow diagram of a process unit for the production of motor fuel in swing bed reactors 8 and 10.

DETAILED DESCRIPTION AND PREFERRED EMBODIMENTS

As previously stated, hydrocarbon alkylation is widely used in the petroleum refining and petrochemical industries to produce a variety of useful acyclic and cyclic hydrocarbon products used as motor fuel, plastic and detergent precursors and petrochemical feedstocks. Much of the installed base of alkylation capacity uses liquid phase hydrofluoric acid, generally referred to as HF, as the catalyst.

The petroleum industry continues to use HF acid as the alkylation catalyst of choice due to the high octane fuel it produces together with other operational advantages. The use of HF in these applications has a long record of highly dependable and relatively safe operation. However, the potential damage from an unintentional release of any sizeable quantity of HF and the need to safely dispose of some by-products formed in product or effluent treating procedures has led to an increasing demand for alkylation process technology which does not employ HF as the catalyst.

It is an objective of this invention to provide a commercially viable alkylation process which does not employ liquid phase HF as the catalyst. It is a further objective of the subject process to provide an alkylation process which counteracts the deactivation of the currently available solid alkylation catalysts. It is a specific objective of the invention to provide a solid bed motor fuel alkylation process for the production of $C_8$ nonlinear hydrocarbons.

The subject invention achieves these objectives by the use of a unique flow scheme that recycles sizeable amounts of the hydrocarbon substrate through a mixed-phase reaction zone that is operated at the boiling point of the liquid phase maintained therein. In preferred embodiments of the invention an alkylation catalyst having a hydrogenation capacity is employed together with circulating hydrogen to selectively hydrogenate $C_6$-plus olefins that are believed at least partially responsible for catalyst deactivation.

It is postulated that a significant portion of the deactivation seen in solid bed alkylation catalysts results from the reaction of the feed olefin(s) to form dimers, trimers or even heavier polymeric entities which clog catalyst pores and/or block catalyst reactive sites. Additionally, these olefins can react further to form diolefinic and cyclic compounds which are found as by-products in liquid phase alkylation. These materials are a portion of what is commonly called acid soluable oil (ASO). Deposition of these materials on the catalyst will also cause rapid deactivation. In order to counteract this mode of deactivation, it is preferred to use an alkylation catalyst which has a weak hydrogenation function which is selective for the hydrogenation of the olefinic dimers and other olefinic "heavy" compounds produced on the catalyst. The use of such a catalyst is however not necessary for the performance of the subject process.

A highly active metal hydrogenation component on the catalyst will hydrogenate the feed olefin. This tendency may be counteracted through the composition of the catalyst and by limiting the hydrogen concentration in the reaction zone. It is therefore preferred that the hydrogen partial pressure in the reaction zone is between 25 and 200 psig and more preferably less than 100 psig. It is further preferred that hydrogen is maintained present in the reaction zone at an inlet concentration equal to less than 10 percent of the concentration of olefinic hydrocarbon present at the inlet to the reaction zone. This is expected to result in the reactor effluent stream having a hydrogen concentration greater than about 0.5 mole percent.

The preferred feed hydrocarbon to the subject process is isobutane, which is then reacted with a normal butene to produce a $C_8$ alkylate for use as gasoline boiling range motor fuel. The feed hydrocarbon or hydrocarbon substrate in this instance may vary to include other hydrocarbons including $C_5$ or $C_6$ paraffins. Another preferred feed hydrocarbon is benzene, which may be alkylated with a wide range of feed olefins including ethylene, propylene and butylene to produce such chemicals as ethylbenzene and cumene. A large amount of benzene is also alkylated with higher carbon number olefins having from about ten to about fifteen carbon atoms per molecule to produce linear alkylbenzenes which are then sulfonated to produce detergents. The feed hydrocarbon is reacted with an alkylating agent which may be chosen from a variety of compounds including monohydric alcohols and olefins. Examples of alcohols which may be employed as the alkylating agent include ethanol and methanol. Methanol, for instance, is widely described in the literature as being useful in the para selective methylation of benzene and toluene. Suitable feed olefins may have from three to five carbon atoms per molecule, with propylene and normal butene being preferred for motor fuel alkylation.

The catalyst used in the process is preferably retained in one or more fixed (nonmoving) beds in a vertical cylindrical reaction zone. The catalyst bed should be provided with an effective means to distribute the entering liquid over the catalyst in a highly uniform manner which results in the surface of all of the catalyst particles being coated with a uniform layer of liquid. The entering liquid phase hydrocarbons are therefore preferably charged to the upper end of the reaction zone via a distributor such as the various perforated deck systems, tubular distributors or spray nozzles known in the art. The catalyst may be retained in a compact cylindrical bed which fills a portion of the reactor vessel but it is preferred that the catalyst is retained in a system which promotes vapor liquid contact and liquid distribution. A preferred system is shown in U.S. Pat. No. 5,073,236 issued to A. P. Gelbein et al. which is incorporated herein for its teaching as to a means to provide uniform liquid-vapor contact in a column-like structure.

The overall process flow of the subject invention is best described by reference to the Drawing. The Drawing is a simplified flow of the motor fuel alkylation embodiment of the invention in which a vapor phase first feed stream comprising normal butenes from line 1 is passed into the reaction zone 10. Also passed into this first reaction zone is an admixture, carried by line 6, of a small hydrogen-rich recycle gas stream from line 5, an isobutane-rich liquid phase process stream from lines 2 and 3 and an optional liquid phase recycle stream carried by line 4. As used herein the term "rich" is intended to indicate a concentration of the indicated compound or class of compounds greater than 50 mole percent and preferably greater than 70 percent. The liquid phase process stream of line 4 contains the isobutane and other butanes which are contained in a liquid phase second feed stream charged to the process via line 25. The feed isobutane can enter the process at many other points. The resulting mixture comprising hydrogen, normal butanes and isobutane is passed through line 6 into reaction zone 10, one of two shown as being used in the process.

The optional second reaction zone 8, which is being regenerated at this time, is also represented on the drawing. During regeneration of the catalyst in the second reaction zone a portion of the isobutane from line 3 is passed into the second reaction zone via line 7. In addition to this hydrocarbon flow a sizeable amount of hydrogen from line 32 is passed into the second reaction zone. If desired, recycle reaction zone effluent liquid and isobutane from line 4 may also be passed into the second reactor as additional regenerent media, but this would normally not be practiced as the reaction zone effluent is not a desirable regenerent media. Another alternative regeneration technique is the use of hot hydrogen stripping, which would comprise the passage of heated hydrogen and little if any isobutane into the reaction zone. The best regeneration method is dependent on the catalyst which is being employed. When reaction zone 10 is being regenerated the flow of these regenerent streams will be switched to flow into the first reaction zone.

The passage of the olefin into the reaction zone in a vapor phase stream is intended to inhibit its rapid migration to the active sites of the catalyst thus leading to higher catalyst stability and selectivity. This delay is due in part from the time required for the olefin to first become absorbed into the liquid phase present on the catalyst surface and also from the additional time required for the olefin to then diffuse to the surface of the catalyst. The speed of both of these transport phenomena will be increased by turbulence present in the reactor and in the liquid phase flowing over the catalyst.

The conditions maintained within the reaction zone are chosen to maintain mixed-phase conditions and to promote the alkylation reaction. The passage of the reactant mixture of line 6 downward over the catalyst retained in the reaction zone 10 therefore results in the reaction of the feed isobutane with the feed butene and the production of $C_8$ branched chain paraffins often referred to as alkylate. As the alkylation reaction is exothermic the released heat of reaction will cause some of the isobutane and butanes and an equilibrium amount of alkylate to enter the vapor phase. There is thereby formed a mixed-phase reaction zone effluent stream carried by line 11 which comprises a mixture of $C_8$ product hydrocarbons, excess hydrogen, unreacted isobutane and a small amount of reaction by-products. This effluent stream is passed through line 12 and an optional but preferred indirect heat exchanger 13 which is employed to heat the reaction zone effluent stream. The heating is intended to cause a larger percentage of the isobutane, which is recycled, to flash into vapor rather than remaining as liquid sent to the product recovery zone. The effluent stream is then passed into a vapor-liquid separation zone 14, which may be operated at a pressure slightly below that in the reaction zone. The combination of a higher temperature and reduced pressure is preferably controlled to cause some additional vaporization of the reaction zone effluent stream and a flash separation of the effluent stream. The effluent stream is thereby separated into a vapor-phase stream carried by line 15 which is rich in isobutane and a liquid phase stream carried by line 22 which has a much higher concentration of the product $C_8$ product hydrocarbon. In this way a portion of the sensible heat content of the effluent stream is used to separate and recycle the isobutane.

A small portion of the vapor phase stream of line 15 may be discharged from the process via line 16 as a means to vent off light gases such as propane which enter the process as impurities in the feed streams. The major second portion of the vapor phase stream of line 15 is passed through lines 17 and 19 into an indirect heat exchange means 20 used to cool and cause a partial condensation of the vapor phase stream. This produces a second mixed-phase stream which is then separated in the vapor-liquid separator 21 into a hydrogen rich second vapor phase stream carried by line 30 and an isobutane rich liquid phase stream carried by line 3. The vapor stream is pressurized in the compresser 31 and then divided into the two portions flowing through lines 32 and 5. The liquid phase stream is pressurized in pump 33 and then passed into the first reaction zone 10 and, if desired, into the second reaction zone 8 when it is undergoing regeneration.

In the depicted embodiment the liquid-phase stream removed from the vapor-liquid separator 14 via line 22 is divided into a smaller first portion which is recycled to the reaction zone 10 via lines 24, 4 and 6 and a larger second portion which is passed via line 23 into the product recovery zone comprising fractionation column 28. Makeup feed isobutane is charged into the process via line 25 and is then passed into the reaction zone via line 4. The liquid-phase stream of line 23 will primarily contain the product hydrocarbon and any heavier by-products of the alkylation reaction such as butene dimers or trimers and will also contain an equilibrium concentration of all of the lighter hydrocarbons present in vessel 14 including isobutane and normal butane. The liquid-phase stream is passed into the fractional distillation column 28 which is operated at conditions effective to separate the entering hydrocarbons into a net overhead stream removed via line 26 which is rich in propane and a net bottoms stream removed in line 27 which is rich in the $C_8$ product hydrocarbon. Also removed from this column, which is referred to in the art as an isostripper, is a sidecut stream of line 29 comprising most of the normal butane which enters the process in the feed streams and a normally vapor phase sidecut stream of line 18, which is rich in isobutane. The isobutane sidecut stream is preferably recycled to the reaction zone via line 19.

While the reaction is being performed in the reaction zone 10, the optional second reaction zone 8 is preferably being regenerated, if regeneration of the catalyst is necessary. Depending on the catalyst and the reaction it may not be necessary or desired to utilize two or more reactors in swing bed mode of operation. However, the presently availble motor fuel alkylation catalysts make it necessary to employ this mode of operation or some mode of onstream regeneration. The exact manner of the regeneration does not form a step in the subject process but is expected to include "washing" the catalyst with a liquid phase hydrocarbon such as isobutane or benzene, possibly at an elevated temperature and in the presence of some hydrogen to remove carbonaceous deposits. The catalyst may, if necessary be contacted with a combustion supporting gas such as air, nitrogen diluted air or ozone to periodically oxidize the carbonaceous deposits which cannot be removed by contact with a liquid phase hydrocarbon. It is desired to employ a hydrocarbon already present in the process as the regenerent. Of the streams available in the process a stream which is rich in $C_4$ hydrocarbons and has a low concentration of olefins and product hydrocarbons is preferred. As already mentioned regeneration may include a hot hydrogen stripping step. Some alkylation catalysts may have isomerization activity, especially at higher regeneration temperatures. In that instance normal butane from the isostripper would be a preferred regenerent.

The regeneration procedure is preferably performed at a higher temperature than the alkylation reaction and in the presence of a higher concentration of hydrogen. Regeneration conditions for the subject process preferably include a temperature of from about 100 to about 150 degrees centigrade. By admixing the high temperature isobutane and hydrogen removed from the reactor in line 9 as regeneration media with the reaction zone effluent of line 11 the reaction zone effluent is heated. This causes a greater degree of vaporization in the separation zone 14 and provides a better recovery of isobutane for recycling. This in turn facilitates the utilization of high isobutane recycle rates and high isobutane to olefin ratios in the reaction zone.

One embodiment of the invention may accordingly be characterized as a process for the alkylation of a feed hydrocarbon which comprises the steps of passing a first feed stream comprising a $C_4$-$C_7$ feed hydrocarbon and a second feed stream comprising a $C_3$-$C_5$ olefinic hydrocarbon into a reaction zone containing a fixed bed of solid liquid coated alkylation catalyst and operated at alkylation-promoting conditions which include an inlet pressure and temperature which result in mixed-phase conditions in which at least a portion of the olefinic hydrocarbon is present as a vapor and reacting the feed hydrocarbon and the olefinic hydrocarbon to produce a branched paraffin product hydrocarbon in an exothermic reaction which causes the vaporization of liquid phase hydrocarbons present in the reaction zone; passing a mixed-phase effluent stream comprising said feed hydrocarbon and said product hydrocarbon, and which is withdrawn from the reaction zone, into a vapor-liquid separation zone in which the effluent stream is separated into a liquid phase process stream, which comprises the product hydrocarbon, and a vapor phase process stream, which is rich in the feed hydrocarbon; passing at least a first portion of the liquid phase process stream into the product recovery zone and optionally passing a second portion of the liquid phase process stream into the reaction zone, and recovering the product hydrocarbon; partially condensing the vapor-phase process stream and thereby producing a second liquid phase stream, which is rich in the feed hydrocarbon, and a second vapor phase stream; and passing a least a major portion of the second liquid phase process stream into the reaction zone.

A preferred embodiment of the subject invention can accordingly be characterized as a process for the alkylation of a feed isoparaffin which comprises the steps of passing a liquid phase first feed stream comprising a $C_4$-$C_7$ feed isoparaffinic hydrocarbon and a vapor phase second feed stream comprising a $C_3$-$C_5$ olefinic hydrocarbon downward through a first reaction zone containing a bed of a solid alkylation catalyst and operated at alkylation-promoting conditions which include the presence of hydrogen at a concentration greater than 0.5 mole percent and an inlet pressure and temperature which result in mixed-phase conditions and reacting the feed hydrocarbon and the olefinic hydrocarbon to produce a branched paraffinic product hydrocarbon in an exothermic reaction which causes the vaporization of liquid phase hydrocarbons present in the first reaction zone; removing a mixed phase effluent stream comprising vapor phase hydrogen, said feed hydrocarbon and said product hydrocarbon from the first reaction zone, and passing the effluent stream into a vapor-liquid separation zone in which the effluent stream is separated into a first liquid phase process stream, which comprises the product hydrocarbon, and a first vapor phase process stream comprising hydrogen and rich in the feed isoparaffinic hydrocarbon; recycling a first portion of the first liquid phase process stream into the first reaction zone and passing a larger second portion of the first liquid phase process stream into a product recovery zone, and recovering the product hydrocarbon; partially condensing the first vapor phase process stream and thereby producing a second vapor phase process stream, which is rich in hydrogen, and a second liquid phase process stream, which is rich in the feed hydrocarbon, and recycling at least a first portion of the second liquid phase process stream to the first reaction zone and passing at least a second portion of the second liquid phase reaction zone into a second reaction zone which is undergoing a catalyst regeneration procedure; passing a minor portion of the second vapor-phase process stream into the first reaction zone and passing a major portion of the vapor-phase process stream into the second reaction zone; and, passing an effluent stream removed from the second reaction zone into the vapor-liquid separation zone in which the effluent of the first reaction zone is separated.

The subject process can be performed using any solid or heterogeneous catalyst which is relatively stable at the conditions needed to maintain mixed-phase fluids in the reactor and has the required activity and selectivity for the desired reaction. A large number of alkylation catalysts have been proposed for the production of motor fuel including various zeolites and superacid catalysts. For instance, U.S. Pat. No. 4,384,161 describes the use of a large pore zeolite and a Lewis acid. The zeolites referred to include ZSM-4, ZSM-3, and the faujasites including zeolite Y and mordenite. The Lewis acids mentioned in this reference include boron trifluoride and aluminum chloride. The alkylation of isoparaffins using a somewhat similar catalyst system comprising a large pore crystalline molecular sieve such as a pillared silicate or an aluminophosphate or silicoaluminophosphate together with a gaseous Lewis acid is disclosed in U.S. Pat. No. 4,935,577. The use of these Lewis acids is not preferred in the subject process as they provide their own waste handling and safety problems. They also will probably require provisions for the circulation of the Lewis acid, which may complicate the process as shown by the just cited U.S. Pat. No. 4,935,577. U.S. Pat. No. 4,377,721 describes the use of ZSM-20 as a motor fuel alkylation catalyst. U.S. Pat. No. 5,157,200 describes an isoparaffin alkylation process using a catalyst comprising a crystalline transition alumina, preferably eta or gamma alumina, which has been treated with a Lewis acid under anhydrous conditions. Previously referred to U.S. Pat. No. 5,157,196 describes an isoparaffin alkylation process using a slurried solid catalyst, with the preferred catalyst being an acid washed silica which has been treated with antimony pentafluoride. Both of these last two references describe a number of prior art solid bed paraffin alkylation catalysts.

Silicalites have been described as useful alkylation catalysts for the production of monoalkylbenzenes in U.S. Pat. No. 4,489,214 to J. R. Butler et al. and as useful in methylating toluene to produce paraxylene in U.S. Pat. No. 4,444,989 assigned to F. E. Herkes. The use of ZSM-5 zeolites in aromatic alkylation is described in U.S. Pat. No. 3,751,506. ZSM-5 zeolites that have been treated with one or more compounds or elements to improve their selectivity for para-selective alkylation of aromatic hydrocarbons are described in U.S. Pat. No. 4,420,418. The use of zeolite L, zeolite Omega and zeolite beta as alkylation catalysts for the selective alkylation of benzene is described in U.S. Pat. No. 4,301,316. The use of a number of natural and synthetic zeolites including clinoptilolite and zeolite Y is described in U.S. Pat. No. 3,251,897. These references give guidance in both the composition and usage of the the catalysts.

A preferred paraffin alkylation catalyst comprises a refractory inorganic oxide impregnated with a monovalent cation, especially an alkali metal cation or an alkaline earth metal cation, and whose bound surface hydroxyl groups have been at least partially reacted with a Friedel-Crafts metal halide. Isomerization analogs of these catalysts without the monovalent metal cations are described in U.S. Pat. Nos. 2,999,074 and 3,318,820 which describe preparation techniques which can be applied to the preferred catalysts. The refractory oxide is preferably alumina having a surface area greater than 50 $m^2/g$, but the use of other oxides including titania, zirconia, silica, boria and aluminum phosphate is contemplated. The preferred catalyst also contains a metal component active for olefin hydrogenation deposited on the inorganic oxide prior to reaction of the bound surface hydroxyl groups with metal halides. This metal may be chosen from the group consisting of nickel, platinum, palladium, rhenium, and ruthenium with the first four of these metals being preferred. The one or more monovalent metal or alkaline earth metal cations in the catalyst may be selected from the group consisting of lithium, sodium, potassium, cesium, silver, copper, beryllium, magnesium, calcium and barium. The use of potassium to reduce the acidity of the catalyst is preferred. Subsequent to the deposition of these metals and the controlled calcination of the composite the composite is reacted with a Friedel-Crafts metal halide. The metal of the halide may be aluminum, zirconium, tin, tantalum, gallium, antimony or boron. Suitable halides are the fluorides, chlorides and bromides.

Operating conditions suitable for use in the reaction zone of the subject process with the preferred catalyst include a temperature of about 4 to about 60 degrees C. (40–140 degrees F.), preferably 15 to 43 degrees C., and a pressure as required to maintain at least a portion (greater than 50 mole %) of the feed hydrocarbon present as a liquid. The olefin weight hourly space velocity (WHSV) should be less than 2.0 $hr^{-1}$ and preferably less than about 1.0.

It is generally preferred that the process is operated with an excess of the feed hydrocarbon compared to the alkylating agent. That is, it is preferred to operate with a ratio of the aromatic hydrocarbon to a feed olefin greater than 1:1, and preferably from about 2:1 to about 5:1 as measured by the flow rates into the reaction zone. Likewise it is preferred to operate with an abundance of isoparaffin compared to alkylating agent in a motor fuel alkylation process. Specifically, it is preferred that the molar ratio of isoparaffin to olefin being charged to the reaction zone is greater than 2:1 and more preferably greater than 3:1. Ratios up to 100:1 are contemplated as being desirable for longer catalyst life between regenerations. It is recognized that the conditions maintained in the subject mixed-phase reaction zone may influence the paraffin:olefin ratio in the liquid phase at the catalyst surface.

Provisions may be made for removing catalyst from the reaction zone in order to regenerate the catalyst and for the addition of fresh or regenerated catalyst. One such system for this is described in U.S. Pat. No. 4,973,780 to R.C. Johnson et al.

What is claimed:

1. A process for the alkylation of a feed hydrocarbon which comprises the steps:

(a) passing a first feed stream comprising a paraffinic feed hydrocarbon and a second feed stream comprising an alkylating agent into a reaction zone containing a fixed bed of solid alkylation catalyst and operated at alkylation-promoting conditions which include an inlet pressure and temperature which result in mixed-phase conditions at which at least a portion of the alkylating agent and the feed hydrocarbon are present as a vapor and reacting the feed hydrocarbon and the alkylating agent to produce a product hydrocarbon in an exothermic reaction which causes the vaporization of liquid phase hydrocarbons present in the reaction zone;

(b) passing a mixed-phase effluent stream comprising said feed hydrocarbon and said product hydrocarbon, and which is withdrawn from the reaction zone, into a separation zone in which the effluent stream is separated into a liquid phase process stream, which comprises the product hydrocarbon, and a vapor phase process stream, which comprises the feed hydrocarbon;

(c) passing a first portion of the liquid phase process stream into a product recovery zone, and recovering the product hydrocarbon;

(d) recovering at least a portion of the feed hydrocarbon from the vapor phase process stream and passing the thus recovered feed hydrocarbon into the reaction zone.

2. The process of claim 1 further characterized in that hydrogen is maintained present in the reaction zone at an inlet concentration equal to less than 10 percent of the concentration of olefinic hydrocarbon present at the inlet to the reaction zone.

3. The process of claim 1 further characterized in that the effluent stream is heated before passage into the separation zone.

4. The process of claim 3 further characterized in that the feed hydrocarbon is recovered from the effluent stream by partially condensing a vapor stream separated from the effluent stream, and then performing a vapor-liquid separation step which produces a liquid phase process stream, which is passed into the reaction zone, and a hydrogen rich vapor stream.

5. The process of claim 1 further characterized in that the second feed stream is passed into the reaction zone as a vapor phase stream and the first feed stream is passed into the reaction zone as a liquid phase stream.

6. The process of claim 1 further characterized in that a second portion of the liquid phase stream recovered from the effluent stream is passed into the reaction zone.

7. A process for the alkylation of a feed hydrocarbon which comprises the steps:

(a) passing a first feed stream comprising isobutane or isopentane as a feed hydrocarbon and a second feed stream comprising a $C_3$-$C_5$ olefinic hydrocarbon into a reaction zone containing a fixed bed of solid liquid coated alkylation catalyst and operated at alkylation-promoting conditions which include an inlet pressure and temperature which result in mixed-phase conditions in which at least a portion of the olefinic hydrocarbon is present as a vapor and reacting the feed hydrocarbon and the olefinic hydrocarbon to produce a branched paraffinic product hydrocarbon in an exothermic reaction which causes the vaporization of liquid phase hydrocarbons present in the reaction zone;

(b) passing a mixed-phase effluent stream comprising said feed hydrocarbon and said product hydrocarbon, and which is withdrawn from the reaction zone, into a vapor-liquid separation zone in which the effluent stream is separated into a liquid phase process stream, which comprises the product hydrocarbon, and a vapor phase process stream, which is rich in the feed hydrocarbon;

(c) passing at least a portion of the liquid phase process stream into a product recovery zone, and recovering the product hydrocarbon;

(d) partially condensing the vapor-phase process stream and thereby producing a second liquid phase stream, which is rich in the feed hydrocarbon, and a second vapor phase stream; and, (e) passing a least a major portion of the second liquid phase process stream into the reaction zone.

8. The process of claim 7 further comprising the step of heating the effluent stream prior to passage into the separation zone.

9. The process of claim 7 further characterized in that hydrogen is present in the reaction zone and in the effluent stream, with the hydrogen concentration in the effluent stream being at least 0.5 mole percent.

10. A process for the alkylation of a feed isoparaffin which comprises the steps:

(a) passing a liquid phase first feed stream comprising a $C_3$-$C_5$ feed isoparaffinic hydrocarbon and a vapor phase second feed stream comprising a $C_3$-$C_5$ olefinic hydrocarbon downward through a first reaction zone containing a bed of a solid alkylation catalyst and operated at alkylation-promoting conditions which include the presence of hydrogen at a concentration greater than 0.5 mole percent and an inlet pressure and temperature which result in mixed-phase conditions and reacting the feed hydrocarbon and the olefinic hydrocarbon to produce a branched paraffinic product hydrocarbon in an exothermic reaction which causes the vaporization of liquid phase hydrocarbons present in the first reaction zone;

(b) removing a mixed phase effluent stream comprising vapor phase hydrogen, said feed hydrocarbon and said product hydrocarbon from the first reaction zone, and passing the effluent stream into a vapor-liquid separation zone in which the effluent stream is separated into a first liquid phase process stream, which comprises the product hydrocarbon, and a first vapor phase process stream comprising hydrogen and the feed isoparaffinic hydrocarbon;

(c) passing at least a major portion of the first liquid phase process stream into a product recovery zone, and recovering the product hydrocarbon;

(d) partially condensing the first vapor phase process stream and thereby producing a second vapor phase process stream, which is rich in hydrogen, and a second liquid phase process stream, which is rich in the feed hydrocarbon, and recycling at least a first portion of the second liquid phase process stream to the first reaction zone and passing at least a second portion of the second liquid phase reaction zone into a second reaction zone which is undergoing a catalyst regeneration procedure;

(e) passing a minor portion of the second vapor-phase process stream into the first reaction zone and passing a major portion of the vapor-phase process stream into the second reaction zone; and (f) passing an effluent stream removed from the second reaction zone into the vapor-liquid separation zone in which the effluent of the first reaction zone is separated.

11. The process of claim 10 further characterized in that the alkylation catalyst comprises a metal component having hydrogenation activity.

12. The process of claim 10 further characterized in that the effluent stream removed from the second reaction zone comprises $C_8$ normal paraffins formed by the hydrogenation of butene dimers formed within the alkylation reaction.

13. The process of claim 10 further characterized in that the alkylation catalyst in the second reaction zone is undergoing regeneration at conditions which include a temperature higher than the temperature maintained in the first reaction zone, and in that a regeneration stream is removed from the second reaction zone and admixed into the mixed-phase effluent stream removed from the first reaction zone.

* * * * *